| United States Patent [19] | [11] | 4,227,911 |
|---|---|---|
| Leonard et al. | [45] | Oct. 14, 1980 |

[54] WETTING AGENT AND USE THEREOF IN AGRICULTURE

[75] Inventors: James D. Leonard, Chaska; Michael J. Lewis, Prior Lake, both of Minn.

[73] Assignee: Conklin Company, Inc., Minneapolis, Minn.

[21] Appl. No.: 950,067

[22] Filed: Oct. 10, 1978

Related U.S. Application Data

[63] Continuation-in-part of Ser. No. 769,314, Feb. 17, 1977, abandoned.

[51] Int. Cl.$^3$ ............................................ A01N 25/00
[52] U.S. Cl. .................................... 71/77; 71/DIG. 1
[58] Field of Search ........................ 71/77, 85, DIG. 1

[56] References Cited

U.S. PATENT DOCUMENTS 3,598,565  8/1971  Graves ...................................... 71/77
3,885,950  5/1975  Ehrig et al. ........................... 71/77 X

*Primary Examiner*—Catherine L. Mills
*Attorney, Agent, or Firm*—Merchant, Gould, Smith, Edell, Welter & Schmidt

[57] ABSTRACT

An easily sprayable aqueous composition for stimulating the root development of plants comprises a surface-tension lowering surfactant, an organic liquid solvent; a foam-suppressing agent; and carboxyvinyl polymer with a carboxylic acid equivalent weight above 90. Improved plant growth stimulation is observed when the composition includes a combination of carboxyvinyl polymers of differing equivalent weights. The composition may be applied directly to plant seeds or to plants or the soil surrounding plants by conventional means. The composition may be applied alone or in combination with pesticides, herbicides, fertilizers, irrigation water, and the like.

15 Claims, No Drawings

WETTING AGENT AND USE THEREOF IN AGRICULTURE

This is a continuation-in-part of our co-pending application Ser. No. 769,314, filed Feb. 17, 1977, now abandoned.

FIELD OF THE INVENTION

This invention relates to a wetting agent or surface-active composition and the use of this composition in agriculture or plant development as a nutrient release agent, an aid or stimulant for the growth or development of roots (e.g. assisting the elongation and formation of secondary roots), a soil conditioner, a coating for plant seeds, and an agent for improving the effectiveness of pesticides, herbicides, wet or dry fertilizers, irrigation water, anhydrous ammonia, and the like. An aspect of this invention relates to a composition and method for improving the development of a root system in plants and crops of commercial agricultural importance such as corn (i.e. zea mays), wheat, soybeans, sorghum, sunflowers, and the like. Another aspect of this invention relates to a multi-purpose wetting agent and a method for using this agent which helps crops get the nourishment and protection they need to reach their genetic potential at yield time, e.g. by contributing to superior root development, causing more advanced crop development in early growth stages, encouraging greater formation of secondary hair roots, and increasing real yield at harvest time. Still another aspect of this invention relates to a multi-purpose wetting agent composition for: reducing surface tension in water and other aqueous compositions, assisting in suspension of wettable powders, reducing foam during the application (e.g. spray application) of agricultural chemicals, improving the compatibility of blends of agricultural chemicals, and assisting in improving the uniformity of application (e.g. spray application) of agricultural chemicals. Still another aspect of this invention relates to a water-based wetting agent concentrate, useful as is or at levels of dilution exceeding 1:1 by weight, which concentrate contains a surface tension-lowering surfactant, a foam-reducing agent, and a polymeric carboxylate thickening agent.

DESCRIPTION OF THE PRIOR ART

It has recently been discovered that the carboxyvinyl (i.e. acrylate) polymers from the class of commercially available polymers sold under the trademark "CARBOPOL" by B. F. Goodrich Chemical Company have a plant growth stimulating effect, including an effect whereby the development of a secondary root system is improved for crops such as corn, wheat, and soybeans. This effect was observed when a wetting agent of the following formula was used to improve the effectiveness of agricultural chemicals:

| Ingredient | Percent by Weight |
|---|---|
| Secondary alcohol ethoxylate | 21–22 |
| Propylene glycol | 8.9 |
| Silicone emulsion foam-reducing agent (10% solids) | 8–9 |
| Water | 60.6 |
| Dye | 0.02 |
| "CARBOPOL 941" | 0.1–0.3 |
| NaOH (50% solids) | 0.09–0.25 |

When attempts were made to commercially utilize the above-identified formula as a plant or root growth stimulant, it was found that spray application of the formula (either at full strength or diluted) was impractical, particularly at high application rates such as 8 or more ounces of full strength formula per acre. Even if the conventional ground-spray equipment were provided with a large orifice nozzle (e.g. a "flood jet" nozzle), clogging problems were observed. For example, clogging would almost always occur on the low pressure side of the in-line screen, i.e. the screen inserted in the chemical line upstream from the nozzle to protect the nozzle from suspended matter in the tank or the line. Apparently, the "CARBOPOL 941" resin, which dissolves rather completely in water if neutralized to a pH above 5 or 6 has a tendency to concentrate and coalesce to a gel-like material on the downstream or low pressure side of a foraminous surface through which the aqueous wetting agent system is flowing. This gel-like material has the tendency to form a sufficiently continuous film or layer to bridge over the open spaces in almost any foraminous element which would be useful as an in-line screen. Thus, total blockage of 20-mesh screens has been observed, and it is presently believed that even larger mesh openings would be blocked.

According to U.S. Pat. No. 3,879,317 (Yueh), issued Apr. 22, 1975, the "CARBOPOL" resins have varying molecular weights above 250,000 and equivalent weights below 80 (e.g. about 75). Infrared spectroscopy indicated that the "CARBOPOLS" comprise polymerized acrylic acid. Acrylic acid has an equivalent weight of about 72, and the slightly higher equivalent weight of the "CARBOPOLS" can be accounted for by the presence of a comonomer. According to U.S. Pat. No. 3,879,317, acrylic acid copolymers of the "CARBOPOL" type usually contain at least 90% and, more typically, at least 95% by weight of acrylic acid units and a small percentage of an allylic comonomer such as an alkylallyl saccharide.

Although this invention is not bound by any theory the presence of the comonomer may be important to the effectiveness of "CARBOPOL" in agriculture. The effect of the comonomer upon the screen-clogging effect is presently not fully understood, however.

SUMMARY OF THE INVENTION

It has now been discovered that partial or total replacement of the "CARBOPOL" with an acrylic copolymer having a relatively higher equivalent weight can reduce or even eliminate the aforementioned screen-clogging problem with little or no sacrifice in plant growth stimulating activity. Indeed, partial replacement of the "CARBOPOL" with a suitable amount of relatively high equivalent weight acrylic copolymer can actually enhance the plant growth stimulant activity of the wetting agent formula, which formula can be made sprayable. For convenience of description, the term "acrylic polymer" is used herein, as it is sometimes used in the art (see, for example, U.S. Pat. No. 3,138,520 to Pugh, issued June 23, 1964 and U.S. Pat. No. 3,703,470 to Brennen, issued Nov. 21, 1972) to refer to polymers and copolymers of either acrylic acid itself ($H_2C=CH-COOH$) or its derivatives, including its lower alkyl-substituted analogs (particularly the alpha-alkyl substituted analogs) such as methacrylic acid. Accordingly, the terms "acrylic copolymer" or "acrylic acid copolymer" or "polyacrylic acid copolymer" refer to carboxyvinyl polymers of acrylic acid or lower alkylacrylic acid interpolymerized or copolymerized with one or more comonomers and includes terpolymers and the like. The term "acrylate" is used herein to refer to both the esters of acrylic acid (e.g. lower alkyl acrylates) and salts of acrylic acid (e.g. alkali metal acrylates). Hence, an "acrylate copolymer" or "polyacrylate copolymer" is a polymer of an acrylic acid salt or ester with one or more comonomers.

According to this invention, a sprayable, aqueous, root development stimulating composition comprises the surface-tension lowering surfactant, a water-compatible organic liquid solvent compatible with the surfactant, the silicone foam-suppressing agent, and a blend of two root-development stimulating agents: (a) an acrylic acid copolymer, (for good sprayability, in the acrylate salt form by virtue of a neutralization or partial neutralization) which has an equivalent weight greater than 72 but less than about 90, and (b) an acrylate copolymer having an equivalent weight greater than 90, preferably about 100–150 (also preferably neutralized or partially neutralized for sprayability). In this preferred embodiment, the ratio of copolymer (b) to copolymer (a) can range from about 100:1 to about 1:20, by weight, and optimum results are ordinarily obtained if the ratio is less than 10:1 but greater than 1:1, e.g. 2:1–6:1 by weight. The compositions of this invention can be used in a variety of different methods, whereby the active root development stimulating agents are applied to the plant, to plant seeds, or to a nutrient medium surrounding the plant or plant seed. Conventional ground and aerial sprayers can be used to apply the composition at rates (based on the full strength formula) ranging from 1 ounce per acre to as high as 40 ounces per acre. Rates of application below 5 ounces per acre are normally considered inefficient, and rates in the range of 8–32 ounces per acre are preferred. Surprisingly, significant clogging problems have not been encountered even at rates about 8 ounces per acre. For most spray equipment, some dilution of the full strength formula is preferred, plain water being a suitable diluent medium. The full strength or diluted formula can also be combined with or applied with wet fertilizers, dry fertilizers, anhydrous ammonia, irrigation water, and the like.

DETAILED DESCRIPTION OF THE INVENTION

As noted previously, compositions of this invention particularly well suited to spray application contain a surface-tension lowering surfactant, a water-compatible organic liquid solvent compatible with the surfactant, a silicone-type foam suppressing agent, and the root development stimulating polycarboxylate component. These ingredients will now be described in greater detail.

THE SURFACE TENSION LOWERING SURFACTANT

To be useful in compositions of this invention particularly intended for spray application, the surfactant should be effective in lowering surface tension at high levels of dilution, e.g. from 1:1 to 1,000:1. The preferred surfactants have a reasonably good balance between hydrophobic and hydrophilic character. This balance can be provided through the combination of an oxyalkylene chain containing at least some oxyethylene units with an organic group having a moderately high molecular weight aliphatic, cycloaliphatic, or aromatic residue. For example, this organic group can be a phenol or an aliphatic primary or secondary alcohol.

The phenol preferably has a monocyclic aromatic nucleus which can be substituted, if desired, with long-chain alkyl groups to provide some aliphatic character. The aliphatic primary or secondary alcohol is preferably a higher alkanol. As used throughout this specification, the term "higher", with reference to aliphatic groups (e.g. alkyl substituents), alcohols and other functional group-containing organic compounds having aliphatic residues, and the like is intended to encompass compounds or groups or radicals having 7 or more carbon atoms, e.g. 10–28 carbons. Aliphatic chains (particulary straight chains) having 30–36 carbon atoms or more are known, but it will not ordinarily be necessary to use such lengthy chains.

Thus, the term "lower" (as in "lower alkanol" or "lower alcohol") is used herein to mean compounds or groups having 1 to 6 carbon atoms.

All surface tension-lowering surfactants do not work with equal effectiveness, the presently preferred surfactants being the reaction product of the components comprising a primary or secondary higher alkanol and 2–100 moles of a lower alkylene oxide. At least a portion of the alkylene oxide is ethylene oxide, and the remainder can be a more hydrophobic oxyalkylene-producing oxide such as 1,2-propylene oxide. As is known in the art, tetramethyleneoxide-producing compounds (e.g. tetrahydrofuran) can also be used to make oxyalkylene chains. When ethylene oxide is polymerized with the alcohol to make an alcohol ethoxylate, the length of the oxyethylene chain (i.e. the number of moles of ethylene oxide) can be selected to properly balance the hydrophobic character of the aliphatic portion of the alcohol. If a mixture of ethylene and propylene oxide is used, the oxypropylene units in the oxyalkylene chain make some contribution to the hydrophobic character of the molecule, thus allowing for greater flexibility in the selection of the alcohol and the length of the oxyalkylene chain. As is known in the art, the oxyethylene and oxypropylene units in the oxyalkylene chain can be arranged randomly or in blocks.

Among the preferred alcohol ethoxylates are the secondary alcohol ethoxylates having the following formula:

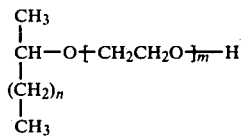

wherein
m is a number ranging from about 2 to about 20 (e.g. 3–12); and
n is a number ranging from 6 to 15 (e.g. 8–12).

Compounds of this general type are commercially available as members of the "TERGITOL S" series (trademark of Union Carbide), e.g. "TERGITOL" nonionic 15-S-3, 15-S-5, 15-S-7, 15-S-9, and 15-S-12. Those "TERGITOLS" which have cloud points are generally found to have a cloud point in 1.0% aqueous solution ranging from about 35° to about 90° C., depending upon the length of the oxyethylene chain and the test method used to determine the cloud point. These surfactants are substantially neutral, a typical pH in 1% solution ranging from 6 to 8 at 25° C.

Although the "TERGITOLS" are preferred, presently available data indicate that any poly(lower alkoxylate) of a higher alkyl-containing alcohol can be substantially equivalent if it has surface-tension lowering properties similar to the "TERGITOLS" and has similar compatibility properties. Commercially available compounds can meet these criteria, particularly when the higher alkyl-containing alcohol is a $C_{22}-C_{26}$ primary alcohol and the oxyalkylene chain contains both oxyethylene and oxypropylene units. Alkoxylates of straight chain alkanols having 12-22 carbons are also suitable in combination with different amounts or ratios of ethylene oxide and propylene oxide.

WATER-COMPATIBLE ORGANIC LIQUID SOLVENTS

Since the sprayable compositions of this invention are aqueous or water-based, some slight tendencies toward phase separation or other incompatibility problems may be encountered with some alkoxylates of higher alkyl-containing alcohols and/or with other ingredients of the composition. However, water in combination with a cosolvent or coupling agent has been found to provide adequate solvent characteristics for all of the ingredients normally contemplated for use in compositions of this invention. Thus, the cosolvent can also be considered to be a "coupling agent". Preferred cosolvents or coupling agents are miscible with water in all proportions and also compatible with the aforementioned surfactants (e.g. the alkoxylates of higher alkyl-containing alcohols). All water-miscible organic liquid solvents do not work with equal effectiveness, and it is generally preferred that the cosolvent have hydroxide functionality and a relatively low molecular weight; thus, mono- or polyfunctionality lower alcohols are particularly effective as cosolvents or coupling agents. Among these are the lower alkanols and lower alkadiols. Maximum water miscibility is obtained with $C_1$-$C_4$ alcohols (methanol, ethanol, isopropyl alcohol, etc.); ethanol (including completely denatured ethanol) and isopropyl alcohol are most convenient from the standpoint of availability and low toxicity. Of the glycols (alkadiols, alkatriols, etc.), ethylene glycol and propylene glycol are particularly preferred.

THE FOAM-SUPPRESSING AGENT

As is known in the art, blending of certain surfactants into certain aqueous systems tends to produce foam. Perhaps even more important from the standpoint of this invention, foam can also be produced when such compositions are applied to crops by means of a spray application. Foam is normally undesirable for a variety of reasons and can be inhibited by including relatively small amounts of foam inhibiting or foam suppressing chemicals in the composition during manufacture. Certain surface active agents, generally known as "defoamers" are known to have a marked foam-reducing effect, just as other types of surface active agents are known to increase foaming. Although the mechanism of defoaming is not precisely understood, it is believed to involve deduction of the film strength of a bubble, thereby facilitating the collapse of a foam.

One particularly effective technique for inhibiting foam formation involves the use of silicone, i.e. organic polysiloxanes. Although the polysiloxanes (e.g. dimethyl polysiloxane) are not soluble in water, they are available in the form of emulsions containing, for example, 10%, 20%, 30%, etc. of polysiloxane. These emulsions are easily dispersed in aqueous systems and remain stably dispersed thereafter. Like most emulsions, amounts less than 40% "solids" by weight can favor the formation of a stable oil-in-water system. It appears to be unnecessary to reduce the "solids" content below 5%, since excellent results have been obtained with commercially available 10% and 30% emulsions. (The term "solids" is used in a manner similar to its use in paint chemistry, wherein all non-volatiles are considered to be "solids".)

THE ROOT-DEVELOPMENT STIMULATING POLYACRYLIC ACID (POLYACRYLATE) SALTS

It is difficult to theorize concerning the activity of agents for stimulation of the elongation and formation of roots systems of agriculturally significant plants such as corn, soybeans, wheat, and the like. In appropriate environments acrylic copolymers have been found by us to have significant activity. This activity has been observed in aqueous solutions containing a wide range of concentrations of a polyacrylate copolymer (e.g. in aqueous solutions containing a few ppm of polyacrylate copolymer and in aqueous solutions saturated with polyacrylate copolymer) without the presence of other chemicals. These polyacrylate copolymers can be crosslinked or non-crosslinked (i.e. essentially linear), but it is believed to be important to the sprayability of the aqueous root-development stimulating composition that at least some of the acrylic acid copolymer component of the composition be essentially linear (non-crosslinked). It is well known that polyfunctional, ethylenically unsaturated monomers can provide the crosslinked character of acrylic copolymers, since crosslinking can occur through the unsaturation. The allyl group, for example, can be introduced into the polymer chain in the manner and for the reasons described in British Pat. No. 870,994 (Rohm & Haas Co.), published June 21, 1961, page 4, line 113 through page 5, line 117. Of the crosslinking agents described in this portion of British Pat. No. 870,994, one should select those which do not interfere with the plant growth stimulating activity of the polymer. No poly lower alkenyl saccharide is mentioned in British Pat. No. 870,994, but a poly alkenyl saccharide (a poly allylic ester) is reportedly present in one or more "CARBOPOLS." In the case of the "CARBOPOLS" the comonomer reportedly contains a saccharide or polysaccharide, such as sucrose, starch or the like. Thus, the available hydroxy groups of the saccharide or polysaccharide are etherified with ethylenically unsaturated substituents, such as allyl. Illustrative would be the allyl disaccharide, octaallyl sucrose.

The saccharide moiety is cross-linked into the polymerized acrylic acid (carboxyvinyl) chain through the copolymerizable ethylenically unsaturated, functional group, that is, the alkenyl substituent (e.g., the allyl groups of octaallyl sucrose).

The "CARBOPOLS" are said to have molecular weights ranging from 250,000 up to more than a million (e.g. 4,000,000) and an equivalent weight (i.e. a carboxylic acid equivalent weight or COOH equivalent weight) of less than 80, e.g. about 75, despite the relatively higher molecular weight and lack of acid functionality in the comonomer. That is, the COOH-equivalent weight of the "CARBOPOLS" is typically just slightly above the theoretical value for an acrylic acid homopolymer. The reason for the relatively low equivalent weight is believed to be the relatively high ratio of acrylic acid units to comonomer units. The unneutralized acrylic acid units would have the formula:

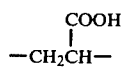

When neutralized, they would have the formula:

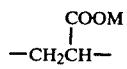

wherein M is typically a monovalent cation, e.g. the ion of an alkali metal or an ammonium (including organic ammonium) cation.

Thus the relatively low equivalent weight of the "CARBOPOLS" indicates a high density of carboxylate (—COOM) sites which help to provide the thickening capabilities of these compounds and also contribute to their water solubility. (Although the "CARBOPOLS" are not, strictly speaking, soluble in water in their non-neutralized or carboxylic acid form, they disperse readily in water, will dissolve in alkaline aqueous media, and will form alkali metal or ammonium salts which generally remain dissolved in water, so long as the pH remains close to or above 7, e.g. above 5.5.)

Although the excellent thickening activity provided by the high density of carboxylate sites can be useful in some contexts, in the present invention it is desired to have good thickening action without the risk of gel formation as the thickened aqueous solution flows through screens which typically are as fine as 40-mesh or 60-mesh or even finer. This gelation phenomenon is not understood, but is presently believed to have some relationship to the density of carboxylate sites, hence the equivalent weight of the polymer, and perhaps also to the slight degree of crosslinked character of the polymer. For this and many other reasons, this invention contemplates the use of acrylic copolymers and combinations of acrylic copolymers which do not form gels on the low pressure or downstream side of the screen. However, the invention also contemplates acrylic copolymer components which equal or exceed uncombined "CARBOPOL" in secondary root development stimulating activity.

It has now been found that a relatively higher equivalent weight polyacrylate copolymer has adequate secondary root-development stimulating activity and also has the ability to reduce or prevent the formation of a gel on the low pressure side of a fine screen. Surprisingly, even if one-third by weight of the acrylic copolymer is still of the "CARBOPOL" type (i.e. the relatively low equivalent weight type), clogging can still be avoided. Perhaps even more surprising, the combination of the low and high equivalent weight acrylic copolymers is found to have enhanced secondary root-development stimulating activity, even though the activity of the combination might be expected to be inferior to an all-"CARBOPOL" formula. Thus, from the standpoint of secondary root development, it is greatly preferred to use a combination of the low and high equivalent weight acrylic copolymers: screen-blocking gels are generally avoided, and root development activity is actually gained rather than lost.

These relatively high equivalent weight copolymers with an equivalent weight greater than 90 useful in the present invention are emulsion copolymers characterized as stable aqueous dispersions, water-insoluble and preferably non-crosslinked, and they are typically water solubilized when neutralized in aqueous media. Examples of this type of copolymer are described in British Pat. No. 870,994. They are prepared by methods well-known in the art of emulsion polymerization wherein a carboxylic acid monomer (A), such as acrylic acid or a lower alkylacrylic acid or a mixture of these is reacted in an aqueous medium with a copolymerizable monomer (B) such as an acrylate ester (typically a lower alkyl acrylate) and with a possible additional neutral monoethylenically unsaturated comonomer (C). The carboxylic acid monomer (A) typically constitutes 25-70% by weight of the copolymer and is usually methacrylic acid, acrylic acid or mixtures thereof. The copolymerizable monomer (B) is typically at least 10% by weight of the copolymer and is constituted by one or more alkyl esters or acrylic or methacrylic acid in which the alkyl group may typically contain up to 12 carbon atoms, but more typically is a lower alkyl acrylate containing, for example, 1 to 4 carbon atoms. Additionally present may be 0 to 40% by weight of one or more other copolymerized neutral monoethylenically unsaturated monomers (C). Thus, the lower alkyl acrylate may make up the entire balance of the emulsion copolymer (i.e. that portion not derived from the carboxylic acid monomer) or a portion of the balance, up to 40% by weight, may be derived from any other neutral monoethylenically unsaturated copolymerizable monomer or mixture thereof. Methyl methacrylate is reported to be the preferred acrylate monomer. The acrylate ester contains no free carboxyl, and the unsaturated monomer (C) preferably can lack free carboxyl also; hence, the COOH equivalent weight of the copolymer is significantly enlarged by the comonomer or comonomers.

The presently preferred commercially available polyacrylic acid copolymer with an equivalent weight in excess of 90 is selected from the "ACRYSOL" ASE series. ("ACRYSOL" is a trademark of Rohm and Haas Company of Philadelphia, Pennsylvania, U.S.A.) This series of copolymers includes "ACRYSOL" ASE 60, 75, 95, and 108, having equivalent weights ranging from 124 to 266, the lowest of these being generally preferred. For example, "ACRYSOL ASE 60" is reported to be a copolymer of methyl methacrylate, ethyl acrylate, and acrylic acid; see U.S. Pat. No. 3,261,796 (Simms), issued July 19, 1966, column 10, line 49 et seq. The following is a comparison of the physical and chemical properties of the preferred "CARBOPOL" ("CARBOPOL 941") and the preferred "ACRYSOL" ("ACRYSOL" ASE 95).

| "CARBOPOL" 941 | "ACRYSOL" ASE 95 |
|---|---|
| Water soluble solid resin supplied in the form of a powder. | Emulsion polymerized, hence supplied in the form of an aqueous emulsion, typically about 20% solids by weight. |
| Supplied in unneutralized (carboxylic acid) form, typically pH of about 3 | Supplied in unneutralized (carboxylic acid) form, pH typically about 3 to 3.3 (1 wt. − % wt. aqueous.) |
| Equivalent weight: near 75 Disperses easily in water. Dispersed particles dissolve when neutralized. | Equivalent weight: 123 to 124 Pre-dispersed in water. Dispersed particles dissolve when neutralized, but may reprecipitate if pH drops to 6 or lower. |
| Thickens water in non-neutralized form. A one weight −% water solution of the sodium salt has a | Minimal thickening of water in non-neutralized form. The 1% aqueous sodium has a Brookfield viscosity |

| "CARBOPOL" 941 | "ACRYSOL" ASE 95 |
|---|---|
| Brookfield viscosity (20 rpm) of at least about 11,000 centipoise (cps) at a pH of 7. | (12 rpm) of 5,600 cps at 25° C. |
| Forms a gel on the downstream side of a 20 to 40 mesh screen when a thickened aqueous solution is flowing rapidly through the screen. | Normally no gel formation on the downstream side of the screen; minimum film forming temperature is greater than 60° C. |

Accordingly, the normally preferred combination of polycarboxylate copolymers used in this invention is as follows:

(1) an acrylic acid copolymer containing 90–99% by weight repeating acrylic untis and at least about 1% by weight of a polyfunctional allylic comonomer, which copolymer has a carboxylic acid equivalent weight above 72 but less than 90 (preferably less than 80), a molecular weight greater than 50,000 (e.g. above 200,000); and (2) an acrylic (including lower alkylacrylic such as methacrylic and ethacrylic) acid-alkyl acrylate copolymer which, in its non-neutralized (carboxylic acid) form has a carboxylic acid equivalent weight about 90 (e.g. 100–270, more preferably 100–150), which, in its non-neutralized (free carboxyl) form is supplied as an emulsion having a pH of 2.7–3.5 and a solids content of about 20%. Dilution of this emulsion (e.g. down to about 5% solids by weight) is not believed to contribute to its stability, the 20% solids level being apparently stable under a variety of conditions such as mechanical shear and freeze-thaw cycles.

Although this invention is not bound by any theory, it is believed that the polyacrylic acid copolymers, at least in neutralized form, have secondary root stimulating activity. It is further believed that when the molecular weight and/or amount of comonomer is insufficient to raise the equivalent weight of the copolymer above 90 and/or the crosslink density is too high, the high density of carboxylate sites or crosslinks in the neutralized form of the copolymer contribute to undesirable in-line gel formation. Reduction of the total available carboxylate sites and/or crosslink density of the combination of acrylic acid copolymers is believed to play a role in reducing this gel formation phenomenon.

Although a variety of bases can be used to neutralize the carboxylic acid form of the polyacrylic acid copolymers used in this invention, there is presently believed to be no advantage in using ammonia or amines to provide the aforementioned —COOM groups. When M is an alkali metal such as sodium or potassium, on the other hand, good efficacy is obtained with less expense. The alkali metal cation can be provided in any conventional manner, such as by neutralization with NaOH, KOH, or basic salts of sodium and potassium (e.g. the carbonates). As between sodium and potassium hydroxide neutralization, slightly better results appear to be achieved with sodium ion. Although the reason for this effect is not understood, it is presently believed that the sodium ion may migrate through soil or other nutrient media with greater ease, at least as compared to potassium ion. In any event, sodium hydroxide and potassium hydroxide are far easier to use from a manufacturing standpoint, particularly as compared to ammonia.

WATER AND OTHER INGREDIENTS

It is not necessary to use deionized water or distilled water in manufacturing compositions of this invention. Tap water, even tap water with a high level of hardness, can be used, provided that appropriate adjustments are made in the addition of base, so that the pH of the concentration will still be in the desired range of less than 9 but greater than 6, e.g. about 7 to 8 at 20°–25° C. Optimum thickening of the composition is achieved with a pH of 7.0–7.5 at 23° C.

The neutralization of the composition can be carried out in the manner of a weak acid-strong base titration, except that almost all of the base (e.g. NaOH) can be added at once after some experience has been gained with the type of tap water in use and/or adequate control over the pH of the water has been obtained. As the vast majority of the base is added, a very small amount can be held back for adjustment to the desired pH. Complete neutralization of all the —COOH sites on the acrylic acid copolymers is not desirable, since, due to the weak acidity of the carboxylic acid group, the resulting salt could have a pH of about 8 or more. Compositions of this invention have adequate viscosity and adequate plant growth stimulating properties at a pH of 8, but a nearly neutral pH provides extra insurance against corrosion of the tank or other spray equipment as well as side reactions with any herbicides, pesticides, fertilizers, or the like which might be added to the composition.

In addition to the aforementioned additional active ingredients (e.g. fertilizers), compositions of this invention can also contain additional inert ingredients such as dyes or other colorants. If the composition contains an ingredient which has a tendency to coalesce or to disperse poorly, inorganic dispersing agents such as the condensed polyphosphates can be included in the composition.

METHOD OF MANUFACTURE

When manufactured at full strength, compositions of this invention typically contain about 50 to about 75% by weight of water. If the polyacrylic acid copolymer is not pre-dispersed in water, the first step is to charge the major portion of the water of a batch to a mixer and add the acrylic acid copolymer powder to the water, so that it can be uniformly distributed (dissolved or dispersed) in the water prior to the addition of other ingredients. The surface tension-lowering surfactant can then be added, followed by a foam inhibiting agent and the cosolvent or coupling agent. Ordinarily, the next-to-last ingredient to be added (assuming the composition contains no other active ingredients such as fertilizers or the like) would be any acrylic acid copolymer emulsions, such as the "ACRYSOL". The composition is then ready for neutralization with base in the manner described previously.

PROPORTIONS

The preferred and optimum proportions of compositions of this invention are set forth in the following Table.

| Ingredient | Amounts in Percent by Weight | |
|---|---|---|
| | Preferred | Optimum |
| Surface-tension lowering surfactant | 10–35 | 20–25 |

-continued

| Ingredient | Amounts in Percent by Weight | |
|---|---|---|
| | Preferred | Optimum |
| Cosolvent | 1-20 | 5-15 |
| Silicone emulsion (5-40% solids by weight) | 1-20 | 1-10 |
| Sodium salt of polyacrylic acid copolymer component* | 0.05-5 | 0.1-1 |
| Water and inert ingredients | Balance | 50-74 |

*Most preferably the aforementioned mixture of high equivalent weight polyacrylic acid-lower acrylate copolymer and low equivalent weight polyacrylic acid-polyfunctional allyl saccharide copolymers.

METHODS OF APPLICATION

ALthough a variety of methods of application can be used, as noted previously, compositions of this invention are particularly well suited to use in conventional ground and aerial spray equipment. Preferred application rates have been discussed previously.

It is ordinarily preferred to dilute a composition of this invention, even though the composition normally already contains a major amount of water. The diluted composition can be sprayed so that it contacts growing plants and/or the nutrient medium in which the plants are planted (e.g. soil). The diluted composition can also be sprayed onto seed beds prior to or after germination.

For ground application, high levels of dilution are desirable, though dilutions with water or more than 1,000 parts by weight of water per part of full strength composition is ordinarily unnecessary. For example, a 40:1 to 200:1 dilution (weight/weight) with water is adequate for most ground applications. For aerial application, dilutions can be considerably less than 40:1, but should be greater than 1:1, e.g. 8 parts water by weight per part of full strength composition.

In methods other than spray application, It is believed that the desired effect of secondary root development stimulation can be achieved with the carboxylate component alone, i.e. the salt of the aforementioned polyacrylic acid copolymers. Among the other preferred techniques of application is the application of the composition directly to a plant seed.

The principle and practice of this invention is illustrated in the following Examples, wherein all parts and percentages are by weight unless otherwise indicated.

EXAMPLE 1

The following formula was found to have excellent secondary root development stimulating activity when applied to crops at the rate of 8-32 ounces per acre.

| Ingredient | Amount in % by Weight |
|---|---|
| Secondary alcohol ethoxylate ("TERGITOL" 15-S-9, trademark of Union Carbide) | 21.7 |
| Propylene glycol | 8.9 |
| Silicone emulsion (30% solids) foam inhibitor ("DOW ANTI-C") | 2.8 |
| Water | 65.3 |
| Dye (Food Drug and Cosmetic green shade 3MT, 5% solids) | 0.02 |
| Acrylic acid copolymer, equivalent weight 75 ("CARBOPOL" 941, trademark of B.F. Goodrich Chemical Co.) | 0.1 |
| Acrylic acid copolymer, equivalent weight 123-124 ("ACRYSOL ASE 95", trademark of Rohm & Haas, 20% solids emulsion) | 1.0 |
| NaOH (50% solids) | 0.18 |

EXAMPLE 2

This is a comparative Example illustrating the beneficial effect of a relatively high equivalent weight polyacrylic acid copolymer on a sprayability and second root development stimulation.

The following two formulas, designed 2-A and 2-B, were tested for sprayability and their sprayability performance compared with the performance of the formula of Example 1

| Ingredient | Amount in % by Weight | |
|---|---|---|
| | Formula 2-A | Formula 2-B |
| "TERGITOL" 15-S-9 (trademark; see Example 1) | 21.7 | 21.5 |
| Propylene glycol | 8.9 | 8.9 |
| Silicone emulsion (10% solids) | 8.6 | 5.4 |
| Water | 60.6 | 60.6 |
| Dye (see Example 1) | 0.02 | 0.02 |
| "CARBOPOL 941", equivalent weight near 75 (see Example 1) | 0.1 | 0.3 |
| NaOH, 50% solids | 0.09 | 0.25 |

At an application rate of 8 to 16 ounces per acre (based on the full strength Formula 2-A or 2-B), both Formulas 2-A and 2-B clogged in an in-line 60 mesh screen in a matter of minutes, due to the formation of a semi-elastic gel-like mass on the low pressure or downstream side of the screen. Formula 2-B clogged the screen in less time than Formula 2-A.

In plant growth tests using laboratory growing conditions, a solution of the sodium salt of "CARBOPOL 941" (see Example 1) was found to be slightly more effective than a similar sodium salt solution of "ACRYSOL ASE-95" (see Example 1) in stimulating development of the secondary root system of the plants. However, the "ACRYSOL ASE-95" was found to be active; moreover, the combination "ACRYSOL ASE-95" and "CARBOPOL 941" at a weight/weight ratio of 2:1-6:1 (37 ACRYSOL": "CARBOPOL") was found to be more active than either acrylic acid copolymer used individually. This ratio varies according to the plant species, and the full range of desirable "ACRYSOL": "CARBOPOL" ranges appears to be much broader (see Section K of Example 4).

The following examples give the results of periodic tests performed under controlled laboratory conditions to compare the root and plant growth stimulating effects on various plants of formulations containing the novel mixture of high equivalent weight polyacrylic acid-lower acrylate copolymer and low equivalent weight polyacrylic acid-polyfunctional allyl saccharide copolymers with that of either of these components used separately. These laboratory tests are used to supply data used primarily for guidance in planning further field testing. Two types of tests are used. Except where otherwise specified the "control" was deionized water.

(Test 1.) Germination on paper:

Seeds are evenly spaced on top of two layers of dampened unbleached paper towel positioned on a sheet of waxed paper. After application of 10 ml of a solution of test material, (by uniform spraying), seeds are covered with two additional layers of towel and the sheets are rolled, fastened and placed vertically in an individual beaker containing deionized water. All tests ware performed at least in duplicate and all rolls from an experiment are placed into a single closed plastic chamber which is then held at 70° F. (21° C.) in the dark for a period of seven to ten days. On termination of the experiment, shoots, primary roots and secondary roots are measured and the fresh and dry weights of roots are determined. Averages of either ten or fifteen seedlings are calculated for each replicate and the values for replicates are then averaged. Statistical evaluation of results is periodically performed.

(Test 2.) Early growth in soil:

Plastic pots with drain holes and removable bottoms are used for these experiments. Seeds are planted in a homogeneous mixture composed of one-third each by volume black dirt, sand and peat. Test solutions are sprayed evenly over the top in 10 ml aliquote prior to watering. Pots are held in a growth chamber for up to six weeks. Illumination is provided by two F96PG17CW flourescent tubes and eight 100 W incondenscent bulbs spaced evenly 2½ feet over the pots (or plants). A 12 hours photo-period is used, temperature is held at 70° F. (21.1° C.) at night and 85° F. (29.4° C.) in the day and daytime relative humidity is maintained between 70 and 75%. On termination, photographic documentation of the foliar and root responses is obtained, root masses are cleaned and weighed and average root wet and dry weights are determined.

EXAMPLE 3

In this example are reported some representative test results using the formula of Example 1, designated as X-1, with Corn (PX-20), Wheat (Era) and Soybean (Evans and Chippewa). In these experiments, a dose of 0.01% is equivalent to a field application of 16 oz./acre.

(A)

Corn, Wheat and soybean seeds treated according to Test 2 with various levels of X-1, corn and wheat for 28 days and soybean for 10 days. Two pots, each containing ten seeds for control and each level of treatment.

| NO. | % X-1 | CORN PLANTS | WHEAT PLANTS | SOYBEAN PLANTS |
|---|---|---|---|---|
| 1 | Control | 16 | 16 | 13 |
| 2 | 0.0001 | 20 | 18 | 15 |
| 3 | 0.001 | 18 | 17 | 13 |
| 4 | 0.01 | 20 | 19 | 12 |
| 5 | 0.1 | 19 | 20 | 15 |
| 6 | 1.0 | 15 | 15 | 20 |

Germination and formation of healthy plants equal to or superior to controls is observed up to 1.0% level of treatment.

(B) Corn seeds treated according to Test 1 for 8 days. The values given are the averages of 15 seedlings. Values for two replicates and the average of these are shown.

| | PRIMARY ROOT LENGTH (MM) | | PRIMARY ROOT WEIGHT (MG.) | |
|---|---|---|---|---|
| REP. | CONTROL | X-1 | CONTROL | X-1 |
| 1 | 230 | 240 | 107 | 109 |
| 2 | 239 | 260 | 115 | 122 |
| AV. | 234 | 250 | 111 | 116 |

(C) Corn seeds treated according to Test 2 for 8 days. Values are averges of 15 seedlings. Values for two replicates and the average of these are shown.

| | PRIMARY ROOT LENGTH (MM) | | PRIMARY ROOT WEIGHT (MG.) | |
|---|---|---|---|---|
| REP. | CONTROL | X-1 | CONTROL | X-1 |
| 1 | 228 | 257 | 102 | 109 |
| 2 | 246 | 261 | 101 | 125 |
| AV. | 237 | 259 | 102 | 117 |

(D) Wheat seeds were treated with two levels of X-1 according to test 1 for 8 days. Values are averages of 10 seedlings. Values for two replicates and the average of these are shown.

| TREATMENT | SHOOT MEASUREMENT (MM.) | PRIMARY ROOT MEASUREMENT (MM.) | SECONDARY ROOT MEASUREMENT (MM.) | AVERAGE NO. OF SECONDARY ROOTS |
|---|---|---|---|---|
| Control | 90 | 212 | 298 | 3.1 |
| 0.005% | 108 | 230 | 336 | 3.4 |
| 0.01% | 104 | 217 | 324 | 3.5 |

(E) Wheat seeds were treated according to Test 2 for 4 weeks with 0.025% of a formula identical to X-1, except that the ACRYSOL:CARBOPOL ratio was 6:1 (1.5 weight % ACRYSOL ASE 95 emulsion to 0.05 wt. % CARBOPOL 941). Three pots, each containing 5 seeds for control and treatment were used. Average values per plant are shown.

| | ROOT WET WEIGHT (MG.) | | ROOT DRY WEIGHT (MG.) | | FOLIAR DRY WEIGHT (MG.) | |
|---|---|---|---|---|---|---|
| REP. | CONTROL | X-1 | CONTROL | X-1 | CONTROL | X-1 |
| 1 | 302 | 415 | 35 | 43 | 99 | 102 |
| 2 | 259 | 400 | 30 | 50 | 73 | 109 |
| 3 | 254 | 398 | 31 | 41 | 101 | 101 |
| AV. | 272 | 404 | 32 | 45 | 91 | 104 |

(F) Chippewa Soybeans are treated with 2 levels of X-1 and germinated on paper according to Test 1 for 7 days. Values are average of 10 seedlings. Values for two replicates and the average of these are shown.

| TREATMENT | SHOOT MEASUREMENT (MM.) | ROOT MEASUREMENT (MM.) |
|---|---|---|
| Control | 158.0 | 171.5 |
| 4 oz./A | 171.5 | 196.5 |
| 64 oz./A | 174.5 | 188.5 |

The data in table A is believed to demonstrate the lack of any apparent toxic effects of X-1 over a wide range of application to corn, wheat and soybeans grown from seed in treated soil. Early stimulation of root growth seems apparent for corn (Tables B & C), Wheat (Tables D & E) and Soybeans (Table F) as well. Two components of X-1, carbopol 941 and acrysol ASE 95 are believed to be agents responsible for this stimulation.

EXAMPLE 4

In this example, further experiments were performed to test the activity of each of these components individually at different and at the same levels of application to seeds germinated on paper according to the previously recited Test 1. They were also tested together in the relative proportions in which they exist in X-1 as well as at widely differing relative proportions with constant total dose. Finally, solutions of complete X-1 and X-1 with either and both active components removed were compared for relative effects on corn growth in soil. Except where indicated, values shown are averages of a minimum of 2 replicates, each resulting from the measurement of 10 seedlings (G) Corn and Soybean seeds are treated with distilled water, 0.00005% Carbopol 941 and 0.0003% Acrysol ASE 95 according to Test 1 for seven days.

| TREATMENT | PRIMARY ROOT LENGTH (MM.) | |
|---|---|---|
| | CORN | SOYBEAN |
| Control | 198.0 | 151.5 |
| Carbopol 941 | 209.5 | 152.5 |
| Control | 215.0 | 137.0 |
| Acrysol ASE 95 | 226.5 | 156.0 |

(H) Wheat seeds are treated with distilled water, 0.0008% Carbopol 941 and 0.005% Acrysol ASE 95 according to Test 1 for seven days.

| TREATMENT | PRIMARY ROOT LENGTH (MM.) |
|---|---|
| Control | 178.5 |
| Carbopol 941 | 185.0 |
| Control | 186.0 |
| Acrysol ASE 95 | 193.0 |

(I) Corn, Soybean and wheat seeds are treated with distilled water and 0.005% Carbopol 941 and Acrysol ASE 95 according to Test 1 for the periods of time shown.

| TREATMENT | PRIMARY ROOT LENGTH (MM.) | | |
|---|---|---|---|
| | CORN 8 DAYS | WHEAT 11 DAYS | SOYBEAN 14 DAYS |
| Control | 239.5 | 215.5 | 255.0 |
| Carbopol 941 | 260.5 | 267.5 | 294.0 |
| Acrysol ASE 95 | 246.5 | 276.0 | 267.0 |

(J) Corn, soybean and wheat seeds are treated with solutions containing different relative ratios of Carbopol 941 and Acrysol ASE 95 with constant combined dose level of 0.005% according to Test 1 for periods of time shown.

| TREATMENT | PRIMARY ROOT LENGTH (MM.) | | |
|---|---|---|---|
| % Carbopol 941 | CORN 9 DAYS | WHEAT 9 DAYS | SOYBEAN 11 DAYS |
| Control | 257.5 | 215.0 | 264.5 |
| 10 | 254.0 | 188.0 | 257.5 |
| 25 | 258.5 | 184.0 | 262.5 |
| 50 | 278.5 | 204.5 | 268.5 |
| 75 | 263.0 | 221.0 | 272.5 |
| 90 | 252.0 | 215.0 | 271.5 |

(K) Corn, wheat and soybean seeds are treated with distilled water, Carbopol 941, Acrysol ASE 95 and both at equivalent of 64 oz. X-1 per acre according to Test 1 for seven days.

| TREATMENT | PRIMARY ROOT LENGTH (MM.) | | |
|---|---|---|---|
| | CORN | WHEAT | SOYBEAN |
| Control | 245.0 | 183.5 | 171.5 |
| Carbopol 941 | 235.5 | 210.5 | 187.0 |
| Acrysol ASE 95 | 244.5 | 205.5 | 196.5 |
| Both | 263.5 | 223.0 | 191.0 |

(L) Corn seeds are treated with 0.05% complete X-1, X-1 with each active component deleted, and with both active components deleted according to Test 2 for 30 days. Values are average of 10 seedings. Values for two replicates and the average of these are shown.

| PRIMARY ROOT WT. (MG) | COMPLETE | DELETED | | |
|---|---|---|---|---|
| | | CARBOPOL 941 | ACRYSOL ASE 95 | BOTH |
| (A.) Fresh Weight per plant | | | | |
| Rep. 1 | 588 | 335 | 465 | 320 |
| Rep. 2 | 682 | 513 | 370 | 417 |
| Average | 635 | 424 | 418 | 368 |
| % of Complete | (100) | 67 | 66 | 58 |

| PRIMARY ROOT WEIGHT (MG) | COMPLETE | DELETED | | |
|---|---|---|---|---|
| | | CARBOPOL 941 | ACRYSOL ASE 95 | BOTH |
| (B.) Dry Weight per plant | | | | |
| Rep. 1 | 38 | 23 | 27 | 20 |
| Rep. 2 | 40 | 35 | 26 | 29 |
| Average | 39 | 29 | 26 | 24 |
| % of Complete | (100) | 74 | 67 | 62 |

The data on tables G and H, appear to show a general stimulation of primary root development in responses to either of the active components of X-1 administered individually at very low levels. Data on tables I and J appear to show that while either active component stimulates root development, with different plants these are relatively different responses to each of the components administered individually at the same level and that the optimum proportion to achieve superior results may be somewhat different for some plants than for others. Data on table K seem to indicate that at levels present in X-1, the stimulation of root development is generally greatest when both active components are present. Data on table L are believed to demonstrate that deletion of either active component produces a lesser root length and weight response in corn than complete X-1 and that response is lower when both components are deleted than when either is present individually.

What is claimed is:

1. In an aqueous composition for stimulating root development of plants, which composition comprises a surface-tension lowering surfactant, a water-compatible organic liquid solvent compatible with said surfactant, a polysiloxane foam-suppressing agent, and one root-development stimulating low equivalent weight solid acrylate copolymer, comprising monomeric units derived from acrylic acid, α-lower alkyl acrylic acid or mixtures thereof, and an allyl saccharide, said monomeric units derived from said acid or acids being in the acrylate salt form; said acrylate copolymer having a molecular weight in excess of 50,000 and a carboxylic acid equivalent weight greater than 72 but less than about 90, the improvement which comprises improving the essentially non-clogging sprayability characteristics of said aqueous composition by means of an essentially non-clogging additive, said essentially non-clogging additive comprising:

a root-development stimulating, second acrylate copolymer uniformly distributed through said aqueous composition, said second acrylate copolymer being a solid, relatively higher equivalent weight acrylic acid copolymer, comprising monomeric units derived from acrylic acid or α-lower alkyl acrylic acid or mixtures thereof, and a lower alkyl acrylate or lower alkyl α-lower alkyl acrylate or mixtures thereof, said relatively higher equivalent weight acrylic acid copolymer having a carboxylic acid equivalent weight greater than 90 and a pH in 1 weight-% aqueous solution of less than about 4; the ratio, by weight, of said second acrylate copolymer to said low equivalent weight acrylate copolymer ranging from about 90:10 to about 10:90.

2. A composition according to claim 1 wherein said second acrylate copolymer is an alkali metal acrylate copolymer formed in situ in said composition by adjustment of the pH of said relatively higher equivalent weight acrylic acid copolymer to greater than 6 but less than about 9 with an alkali metal hydroxide.

3. A composition according to claim 2 wherein said relatively higher equivalent weight acrylic acid copolymer is added to said composition prior to said adjustment of the pH in the form of a stable aqueous emulsion having a pH of 2.7–3.5 and a solids content of at least 5% by weight.

4. A composition according to claim 1 wherein said ratio of said second acrylate copolymer to said low equivalent weight solid acrylate copolymer is at least about 1:1.

5. A composition according to claim 1 having a pH of about 7 to 8 at 23° C. and comprising:
  (a) 10–35% by weight of surface-tension lowering poly(lower alkoxylate) of a higher alkyl-containing alcohol;
  (b) 1–20% by weight of a water-miscible, mono- or polyfunctional lower alcohol;
  (c) 1–20% by weight of de-foaming polysiloxane emulsion having a solids content of at least 5% by weight; and
  (d) 0.05–5% by weight of the alkali metal salts of a mixture of acrylate copolymers, said mixture consisting essentially of:
    1. an acrylate copolymer containing 90–99% by weight repeating acrylate units and at least about 1% by weight of an allyl saccharide comonomer, having a carboxylic acid equivalent weight ranging from 72 to 80, and having a molecular weight above about 200,000;
    2. a second acrylate copolymer having a carboxylic acid equivalent weight in the range of 100–150; essentially the balance of said composition being water.

6. A composition according to claim 5 consisting essentially of:
  (a) 20–25% by weight of an ethoxylated secondary alkanol;
  (b) 5–15% by weight of propylene glycol;
  (c) 1–10% by weight of a dimethyl polysiloxane emulsion containing 5–40% solids by weight;
  (d) 0.1–1% by weight of the sodium salts of said acrylate copolymers; and
  (e) about 50 to 74% by weight of water.

7. A method for improving the development of a plant or plant seed by applying the composition of claim 1 to said plant or plant seed, said applying step being carried out by spraying said composition into the nutrient medium in which said plant or plant seed is planted.

8. A composition according to claim 1, wherein said ratio is at least about 1:1.

9. A composition according to claim 1, wherein said ratio is at least about 2:1.

10. A composition according to claim 1, wherein said ratio ranges from about 2:1 to about 6:1.

11. A method for reducing the clogging of a screen element of a spraying means during the spraying, with said means, of a plant-growth stimulating composition, wherein said plant growth stimulating composition comprises a root-development stimulating low equivalent weight solid acrylate copolymer comprised of acrylic acid, α-lower alkyl acrylic acid or mixtures thereof in the form of a neutralized acrylate salt copolymerized with an allyl saccharide, said monomeric units derived from said acid or acids being in the acrylate salt form; said acrylate copolymer having a molecular weight in excess of 50,000 and a carboxylic acid equivalent weight greater than 72 but less than about 90 distributed through an aqueous medium, said method comprising:

reducing said clogging by including in said composition a root-development stimulating, second acrylate copolymer uniformly distributed through said composition, said second acrylate copolymer being a solid, relatively higher equivalent weight acrylic acid copolymer, comprising monomeric units derived from acrylic acid or α-lower alkyl acrylic acid or mixtures thereof, and a lower alkyl acrylate or lower alkyl α-lower alkyl acrylate or mixtures thereof, said relatively higher equivalent weight acrylic acid copolymer having a carboxylic acid equivalent weight greater than 90 and a pH in 1 weight-% aqueous solution of less than about 4; the ratio, by weight, of said second acrylate copolymer to said low equivalent weight acrylate copolymer ranging from about 90:10 to about 10:90.

12. A method according to claim 11 wherein said second acrylate copolymer is an alkali metal acrylate copolymer formed in situ in said composition by adjustment of the pH of said relatively higher equivalent weight acrylic acid copolymer to greater than 6 but less than about 9 with an alkali metal hydroxide.

13. A method according to claim 12 wherein said relatively higher equivalent weight acrylic acid copolymer is added to said composition prior to said adjustment of the pH in the form of a stable aqueous emulsion having a pH of 2.7–3.5 and a solids content of at least 5% by weight.

14. A method according to claim 12 wherein the said composition, including said second acrylate copolymer after said adjustment of the pH, comprises:
   (a) 10–35% by weight of surface-tension lowering poly(lower alkoxylate) of a higher alkyl-containing alcohol;
   (b) 1–20% by weight of a water-miscible, mono- or polyfunctional lower alcohol;
   (c) 1–20% by weight of de-foaming polysiloxane emulsion having a solids content of at least 5% by weight; and
   (d) 0.05–5% by weight of the mixture comprising the alkali metal salts of said low equivalent weight acrylate and the alkali metal salts of said second acrylate, said mixture consisting essentially of:
   1. an acrylate copolymer containing 90–99% by weight repeating acrylate units and at least about 1% by weight of an allyl saccharide comonomer, having a carboxylic acid equivalent weight ranging from 72 to 80, and having a molecular weight above about 200,000;
   2. a second acrylate copolymer having a carboxylic acid equivalent weight in the range of 100–150; essentially the balance of said composition being water.

15. A method according to claim 11, wherein said ratio is at least about 1:1.

* * * * *